United States Patent [19]

Driller et al.

[11] Patent Number: 5,016,615

[45] Date of Patent: May 21, 1991

[54] LOCAL APPLICATION OF MEDICATION WITH ULTRASOUND

[75] Inventors: Jack Driller, Ridgewood, N.J.; William J. Faulkenberry, Long Island City, N.Y.; Frederic L. Lizzi, Tenafly, N.J.

[73] Assignee: Riverside Research Institute, New York, N.Y.

[21] Appl. No.: 482,313

[22] Filed: Feb. 20, 1990

[51] Int. Cl.$^5$ .................... A61B 17/00; A61M 37/00
[52] U.S. Cl. .................... 128/24 A; 604/20; 604/890.1; 604/891.1; 604/660.03
[58] Field of Search .................... 128/24 A, 660.03; 604/890.1, 891.1, 20

[56] References Cited

U.S. PATENT DOCUMENTS

| | | | |
|---|---|---|---|
| 3,401,690 | 9/1968 | Martin | 604/22 |
| 3,957,650 | 5/1976 | Petrushkin et al. | 210/380 R |
| 4,484,569 | 11/1984 | Driller et al. | 128/24 A |
| 4,582,061 | 4/1986 | Fry | 128/654 |
| 4,683,242 | 7/1987 | Poser | 514/539 |
| 4,725,271 | 2/1988 | Korol | 604/890.1 |
| 4,767,402 | 8/1988 | Kost et al. | 604/20 |
| 4,771,130 | 9/1988 | Cohen | 604/20 |
| 4,780,212 | 10/1988 | Kost et al. | 210/646 |
| 4,787,888 | 11/1988 | Fox | 128/24 A |
| 4,796,637 | 1/1989 | Mascuch et al. | 128/658 |
| 4,863,457 | 9/1989 | Lee | 604/891.1 |

FOREIGN PATENT DOCUMENTS 0654254 3/1979 U.S.S.R. .................... 604/20

OTHER PUBLICATIONS

Wortmann, W. et al., "Phonophoresis as a New Method for Perfusion of the Ovary In Vivo," Abst. No. 77, Acta endocr. (Kbh) Suppl. 173–177 (1973).
Alward, T. M. et al., "Ultrasonic Enhancement of Membrane Permeation of Acetylsalicylic Acid," in Proc. of Thirteenth Annual Northeast Bioengineering Conf., vol. 2, pp. 480–483 (Mar. 12–13, 1987).
Skauen, D. M. et al., "Phonophoresis," Int. J. of Pharmaceutics, vol. 20, pp. 235–245 (1984).
Wing, M., "Phonophoresis with Hydrocortisone in the Treatment of Temporomandibular Joint Dysfunction," Physical Therapy, vol. 62, pp. 32–33 (1982).
Novak, E. J., "Experimental Transmission of Lidocaine Through Intact Skin by Ultrasound," Arch. Phys. Med. & Rehab., vol. 64, pp. 231–232 (1964).
Griffen, J. E. et al., "Ultrasonic Movement of Cortisol into Pig Tissue," Am. J. of Phys. Med., vol. 44, pp. 20–25 (1965).
Griffen, J. E. et al., "Ultrasonic Movement of Cortisol into Pig Tissue," Am. J. of Phys. Med., vol. 42, pp. 77–85 (1963).
Griffen, J. E., et al. "Low–Intensity Phonophoresis of Cortisol in Swine," Phys. Therapy, vol. 40, pp. 1336–1344 (1968).
Griffen, J. E. et al., "Effects of Ultrasonic Frequency on Phonophoresis of Cortisol into Swine Tissue," Am. J. of Phys. Med. vol. 51, pp. 62–78 (1972).
Griffen, J. E. et al., "Patients Treated with Ultrasonic Driven Hydrocortisone and with Ultrasound Alone," Phys. Therapy, vol. 47, pp. 594–601 (1967).
Kleinkort et al., "Phonophoresis with 1 Percent Versus 10 Percent Hydrocortisone," Phys. Therapy, vol. 55, pp. 1320–1324 (1975).

(List continued on next page.)

Assistant Examiner—K. M. Pfaffle
Attorney, Agent, or Firm—Brumbaugh, Graves, Donohue & Raymond

[57] ABSTRACT

A method and an apparatus for applying a therapeutic substance to body tissue are provided in which ultrasonic radiation is used. The method allows the application of medication to be tailored to the needs of an individual patient. In particular, the timing, duration, intensity, and concentration of the application of medication can be adjusted according to individual requirements. Side effects of tissue adjacent to tissue in need of medication are also minimized.

14 Claims, 2 Drawing Sheets

OTHER PUBLICATIONS

Kost et al., "Effect of Ultrasound on Transdermal Drug Delivery," Abstract in 3rd Ann. Mtg., Amer. Assoc. Pharm. Sci. (Orlando, Fla. 1988).

Benson et al., "Influence of Ultrasound on the Percutaneous Absorption of a Range of Nicotinate Esters," J. Pharm. & Pharmocol., vol. 40, Suppl. 40P (Dec. 1988).

Novitsky, I. Y., "Combined Usage of Ultrasound and Dioxidine in Treatment of Infectious Keratitis and Corneal Ulcers".

Kleiman, B. V., "Phonophoresis of Hydrocortisone for Opaque Cornea".

Tsok, R. M., "The Usage of Phonophoresis for Treatment of Diseases in the anterior Segment of the Eye".

Vainshtein, E. S. et al., "Experimental Substantiation and Results of Clinical Use of Lecopaine Phonophoresis in the Treatment of Some Eye Diseases".

Goralchuk, M. V., "Effectiveness of Pencillin Phonophoresis in Purulent Ulcers of the Cornea."

ALZA Corporation brochure "Ocusert (Pilocarpine) Ocular Therapy System", (1984).

*Primary Examiner*—Lee S. Cohen

LOCAL APPLICATION OF MEDICATION WITH ULTRASOUND

The invention described herein was made in the course of work under a grant from the National Institute of Health.

BACKGROUND OF THE INVENTION

This invention relates to the application of a therapeutic substance or of a medication to body tissue. In particular, ultrasonic radiation is used in the application of the therapeutic substance.

Medication may be applied to a target body tissue systemically. However, tissue other than the target tissue is also exposed to the medication which may cause harmful side effects. As a result of diffusion of medication into other tissue during systemic application, the concentration of medication that may be applied to the target tissue is limited.

Accordingly, an object of the invention is to provide a method for applying medication so that higher concentrations of medication may be applied to the target tissue.

A further object of the invention is to provide such an application method to minimize side effects in adjacent tissue.

A further object of the invention is to provide a method whereby medication is locally applied to target tissue and selective heat is simultaneously, locally applied to the same target tissue. Application of heat to elevate the temperature of the target tissue to a non-toxic level can enhance the efficacy of certain mediations. Selective delivery of ultrasound radiation can produce the desirable local temperature elevation.

A further object of the invention is to provide such an application method so that timing, duration, and intensity of the application of medication are tailored to suit the needs of an individual patient.

A further object of the invention is to provide an apparatus for applying therapeutic substance to body tissue.

SUMMARY OF THE INVENTION

In accordance with the invention, there is provided a method for applying a therapeutic substance or medication to body tissue of a person or animal wherein the therapeutic substance is encapsulated in a receptacle having a porous or semiporous surface. The receptacle is positioned with the porous surface adjoining the body tissue. When the receptacle is irradiated with ultrasonic radiation, diffusion of the therapeutic substance through the porous surface of the receptacle accelerates. The therapeutic substance is thereby applied to the targeted body tissue.

In an alternate embodiment, the medication may be contained in a sponge or impregnated foam-like plastic positioned adjoining the target body tissue. In connection with the application of ultrasound, ultrasonic A-scan or B-scan imaging can be used to aid in location of an implanted receptacle and alignment of the ultrasonic beam direction and may also be useful in monitoring the available medication in an implanted receptacle.

Suitable radiation absorbing material, such as radiopaque or sonopaque markers may be provided on the receptacle to permit the position and orientation of the receptacle to be ascertained without direct vision but with standard X-ray or ultrasound visualization equipment.

There is further provided an apparatus for applying a therapeutic substance or medication to body tissue comprising a transducer assembly and a medication capsule. The transducer assembly includes an ultrasonic transducer mounted within an enclosure having an aperture. The transducer and enclosure are arranged so that the transducer radiates ultrasonic energy outwardly from the enclosure through the aperture towards a medication capsule. An aperture of the medication capsule is formed of porous material and is opposite the aperture of the enclosure in the direction of ultrasonic radiation from the transducer.

For a better understanding of the present invention, together with other and further objects, reference is made to the following description, taken in conjunction with the accompanying drawings, and its scope will be pointed out in the appended claims.

DESCRIPTION OF THE PREFERRED EMBODIMENTS

Figure 1:
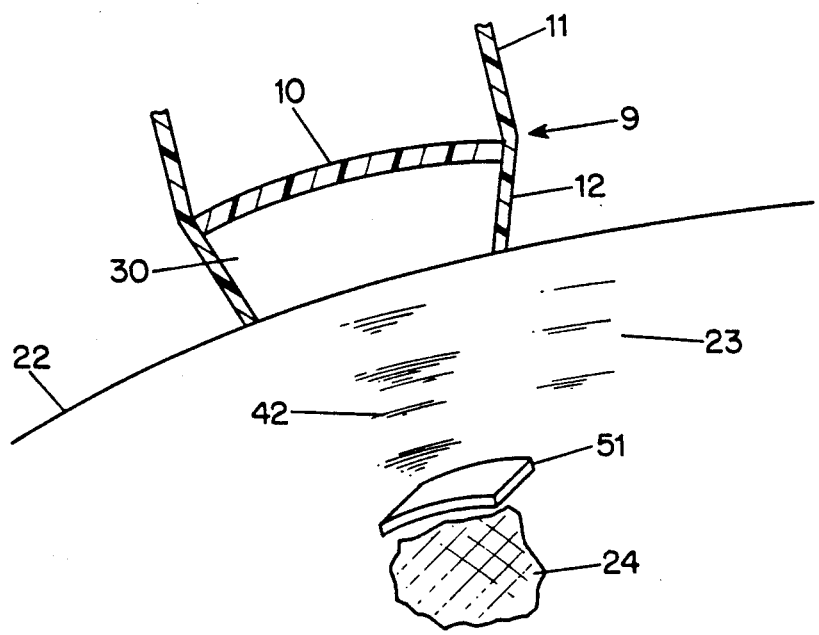
FIG. 1 is a sectional view illustrating practice of a method of the invention for applying medication to internal tissue.

In the embodiment of FIG. 1, a transducer assembly 9 controls the application of medication encapsulated in a receptacle 51 to target tissue 24. The transducer assembly 9 comprises a cylindrical housing portion 11; an ultrasonic transducer in the form of a hollow, spherical section 10; and a truncated conical shell 12. In order to conduct ultrasonic radiation from the transducer 10 efficiently, the cavity of conical shell 12 is filled with a first fluid 30, such as a saline solution or distilled water. Intervening tissue 23 separates the transducer assembly 9 external to body surface 22 from target tissue 24. As indicated by transducer 10 and by wavefronts 42, the ultrasonic radiation may be formed as converging ultrasonic waves directed at an ultrasonic focal point, which is determined by the radius of curvature of the spherical section transducer 10.

Figure 2:
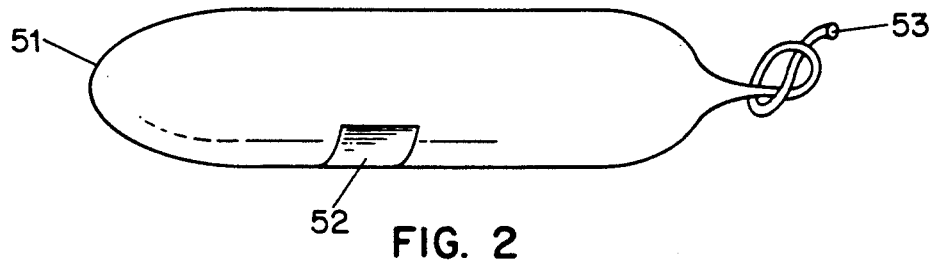
FIG. 2 is a detailed diagram of a receptacle having a surface formed of porous material which is used in connection with practice of the invention.

FIG. 2 provides a more detailed diagram of the receptacle 51. Receptacle 51 may be of any selected shape and is formed as a liquid containing pouch having a generally liquid impervious surface. A porous portion 52, is formed of a porous material having a selected porosity. GORETEX material, manufactured by Gore and Associates and comprising biocompatible porous polytetrafluorethylene, has been found suitable. Medication is supplied to the receptacle 51 through an end 53 which is thereafter sealed. Preferably receptacle 51 is formulated to include suitable radiopaque or sonopaque material to enhance location and imaging of the receptacle and its orientation by conventional X-ray or ultrasound imaging equipment. For example, X-radiation absorbing material may be provided as a portion of the receptacle to thereby permit X-radiation based location of the receptacle.

Referring to FIGS. 1 and 2, receptacle 51 is implanted with the porous portion 52 adjoining target tissue 24. The receptacle 51 may be implanted adjacent to the target tissue 24 following surgical exposure or by a laparotomy-type introduction procedure. Normally, the medication in receptacle 51 will remain in the receptacle or will slowly diffuse out from the porous portion 52. Upon exposure to ultrasonic radiation, the diffusion of medication from the porous portion 52 and onto the target tissue 24 accelerates. The receptacle 51 may be replenished with medication by injecting medication directly into the receptacle 51 or by injecting medication into a filling port which is in fluid communication with the receptacle.

By using a focused beam of ultrasonic radiation, excessive exposure of neighboring tissue 23 to the radiation is avoided. Wavefronts 42 in FIG. 1 indicate that ultrasonic radiation passes through receptacle 51, across porous portion 52, and into target tissue 24 as it accelerates the diffusion of medication into target tissue 24. In addition to accelerating the diffusion of medication, the ultrasonic radiation will generate a localized heating of the target tissue, particularly in the region of the ultrasonic focal point. Such local heating has been shown to increase the efficacy of certain medications.

The arrangement of FIG. 1 is preferably adjusted to provide ultrasonic radiation in a direction which is generally outward with respect to the porous portion 52, preferably in a nearly normal direction. Radiation from transducer 10 may be provided at periodic, adjustable intervals. In this manner, the concentration of medication in target tissue 24 as well as the timing, duration, and intensity of the application of medication can be controlled.

Figure 3:
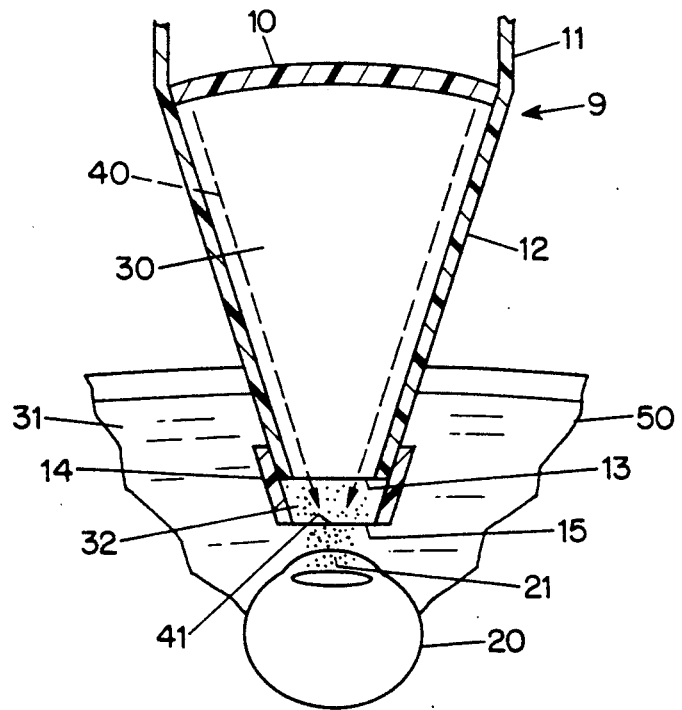
FIG. 3 is a sectional view showing a representative embodiment of an apparatus according to the invention applying medication to an eye.

As illustrated in FIG. 3, an embodiment of an apparatus of the invention may be used in connection with eye treatment. A patient is prepared by placing a drape 50 having a central aperture around an eye 20 which is to be treated. In the particular embodiment of FIG. 3, a cornea 21 or anterior chamber (not numbered) of the eye is the target tissue for medication or therapeutic substance 32 encapsulated within a medication capsule 14. An aperture 13 of the transducer assembly 9 at the truncated end of conical shell 12 forms an upper wall of the medication capsule 14. A porous membrane 15 forms the lower wall of the medication capsule. The medication capsule is immersed in the drape 50 and in the vicinity of the eye 20.

In particular, the drape 50 contains a second fluid 31, such as a saline solution, and the lower wall of the medication capsule is immersed in the second fluid 31. The second fluid 31 provides a conductive path for ultrasonic radiation and allows medication 32 to diffuse to the cornea 21. A suitable material for the porous membrane 15 is GORETEX, and the membrane 15 is close to or in contact with the eye 20. For efficient conduction of ultrasonic radiation from the transducer 10 enclosed in conical shell 12, the cavity of conical shell 12 is filled with a first fluid 30, such as a saline solution or distilled water. A rubber membrane (not numbered) closing the aperture 13 of transducer assembly 9 retains fluid 30 in conical shell 12. Referring to FIG. 3, the medication capsule 14 containing medication 32 surrounds the aperture of transducer assembly 9 and is sealed to the conical shell 12. The porous membrane 15 closes the aperture of medication capsule 14 which is opposite the aperture of transducer assembly 9 and on the axis of conical shell 12.

Using the FIG. 3 apparatus, it is possible to bring porous membrane 15 directly into contact with cornea 21 and thereby directly couple ultrasonic radiation to eye 20, eliminating the need for drape 50 and saline bath 31.

Ultrasonic radiation from transducer 10 follows radiation path 40 enclosed within the cavity of conical shell 12. The radiation travels toward the apex of the conical shell 12 along the cone axis and focuses at a focal point 41 in the vicinity of the porous membrane 15. By using ultrasonic radiation which converges at focal point 41, excessive exposure of body tissue to the radiation is avoided.

Control of the axial location of the medication capsule 14 from the conical shell 12 will cause the focal point 41 to be located in front of, on or behind the porous membrane 15.

Figure 4:
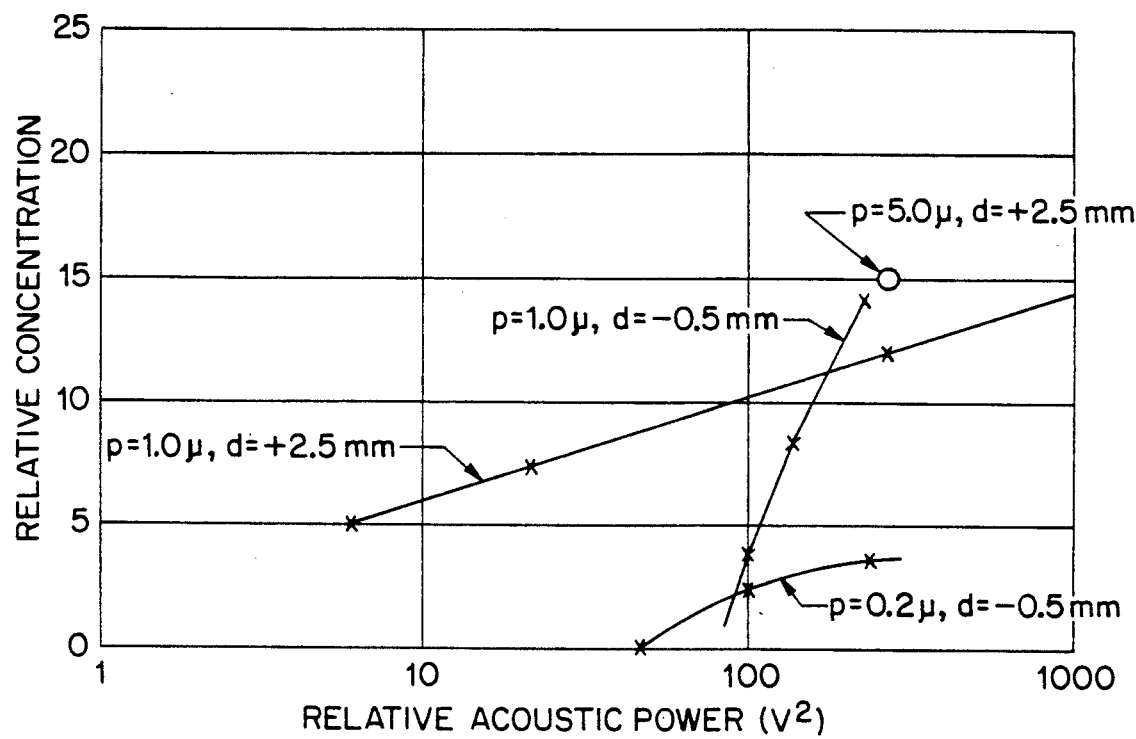
FIG. 4 is a graph showing the relation of flow of a therapeutic substance to radiation intensity and membrane pore size.

FIG. 4 shows the results of experiments which were performed utilizing a transducer/medication capsule assembly of the type shown in FIG. 3 with the objective of measuring the effect of ultrasonic irradiation on diffusion of medication through membranes of various pore size. The tip of the assembly having membrane 15 was immersed in a small receptacle containing protein-buffered saline (PBS). The transducer was a spherical shell transducer with an 80 mm diameter and a 90 mm focal distance (i.e. radius of curvature). The medication chamber 32 was filled with Garamicin. The tests involved a porous membrane of GORETEX, manufactured by Gore and Associates and comprising biocompatible porous polytetrafluorethylene, having pore sizes P of 0.2, 1.0 and 5.0 microns. The focal point location was adjusted to have locations d of 0.5 mm behind the membrane ($-$) and 2.5 mm ($+$) in front of the membrane. Ultrasound energy at 4.68 MHz was applied at various power levels ($V^2$) for five minute intervals after which samples of the PBS were analyzed for quantity of Garamicin. A measured quantity of Coomassie blue was added to each sample to bind and stain available protein. The quantity of Garamicin was then assayed with a calibrated spectrophotometer. The results comprising relative (uncalibrated) concentration of Garamicin as a function of logarithmic power level are shown in FIG. 4. A power level ($V^2$) of 100 corresponds to approximately 2.5 watts total acoustic power. The results demonstrate increased diffusion with increased power and an appropriate pore size of 1.0 micron for Garamicin. The experiment used focused continuous-wave (CW) acoustic energy, but pulsed and/or unfocused acoustic energy can also be used. This data demonstrates that varying the power provided by the external source of ultrasound energy will control the rate at which the medication is released from the receptacle.

While the exemplary embodiments use porous membranes to contain the medication, it is contemplated that a sponge or impregnated plastic, such as polyurethane foam may also be useful for containing the medication prior to application of the ultrasound.

Practice of the invention with respect to implanted receptacles as shown in FIG. 1 may be enhanced by the use of an Ultrasonic Diagnostic and Therapeutic Transducer as described in U.S. Pat. No. 4,484,569 to enable the physician to use A-Scan or B-Scan ultrasonic images for purposes of locating the implanted receptacle and applying effective doses of higher energy therapeutic ultrasonic radiation. Other imaging transducers can also be used for purposes of locating the implanted receptacle.

Although the invention has been described herein with reference to specific embodiments, many modifications and variations of the invention will readily occur to those skilled in the art. Accordingly, all such variations and modifications are included within the intended scope of the invention.

We claim:

1. A method for applying a therapeutic substance to body tissue of a person or animal, comprising the steps of:
   supplying said therapeutic substance in a receptacle having a surface portion formed of porous material having a selected porosity;
   implanting said receptacle in said person or animal with said surface portion adjoining said body tissue; and
   irradiating said implanted receptacle with ultrasonic radiation thereby to cause said therapeutic substance to diffuse through said porous surface portion at a greater rate than in the absence of said radiation and thereby applying said therapeutic substance to said tissue so that the rate of application of said therapeutic substance to said tissue is controlled by the exposure of said receptacle to said ultrasonic radiation.

2. A method as specified in claim 1 wherein said step of supplying said therapeutic substance comprises encapsulating said substance in said receptacle having a surrounding wall wherein said surrounding wall includes said surface portion having a major portion formed of a liquid impervious surface and a minor portion formed of said porous material.

3. A method as specified in claim 1 wherein said step of supplying said therapeutic substance comprises impregnating said therapeutic substance in said receptacle, where said receptacle is in the form of a pad of porous material, said pad having said porous surface portion.

4. A method as specified in claim 1 wherein said ultrasonic radiation has a power level selected to cause simultaneously selective heating of said tissue to elevate the temperature of said tissue to a non-toxic level while causing said therapeutic substance to be applied to the said tissue.

5. A method as specified in claim 1 wherein said ultrasonic radiation is applied in a direction which is perpendicular with respect to said porous surface portion.

6. A method as specified in claim 1 wherein said ultrasonic radiation is reflected from said receptacle and said target tissue in such a manner as to produce ultrasonic images selected from the group consisting of A-Scan and B-Scan ultrasonic images, and wherein said images are used to monitor one or more conditions selected from the group consisting of ultrasonic beam orientation with respect to said receptacle, position of said receptacle, orientation of said receptacle, tissue response to said therapeutic substance, and available supply of therapeutic substance in said receptacle.

7. A method as specified in claim 1 wherein said step of irradiating is repeated at periodic intervals.

8. A method as specified in claim 1 further comprising the step of replenishing said therapeutic substance in said receptacle.

9. A method as specified in claim 1 further comprising providing radiopaque material in small discrete portions of the surface of said receptacle, thereby permitting the location and imaging of said receptacle with conventional X-radiation imaging equipment.

10. A method as specified in claim 1 wherein the power of said ultrasonic radiation is varied thereby to vary the rate of diffusion of said therapeutic substance.

11. A method as specified in claim 1 wherein said therapeutic substance is applied to said tissue so that higher concentrations of said therapeutic substance are applied to said tissue in comparison with systemic application of said therapeutic substance.

12. A method as specified in claim 1 further comprising providing sonopaque material in small discrete portions of the surface of said receptacle, thereby permitting the location and imaging of said receptacle with conventional ultrasound imaging equipment.

13. A method of applying a therapeutic substance to body tissue of a person or animal, comprising the steps of:
   encapsulating said therapeutic substance in a receptacle having a surface portion formed of porous material having a selected porosity;
   positioning said receptacle adjacent said body tissue with said porous surface portion adjoining said body tissue; and
   passing ultrasonic radiation through said receptacle, across said surface portion and into said tissue thereby to diffuse said therapeutic substance into said tissue so that the rate of application of said therapeutic substance to said tissue is controlled by the exposure of said receptacle to said ultrasonic radiation substance.

14. A method as specified in claim 13 wherein said therapeutic substance is applied to said tissue so that higher concentrations of said therapeutic substance are applied to said tissue in comparison with systemic application of said therapeutic substance.

* * * * *